US00PP31198P3

(12) United States Plant Patent
Zlesak

(10) Patent No.: US PP31,198 P3
(45) Date of Patent: Dec. 10, 2019

(54) ***PHYSOCARPUS* PLANT NAMED 'ZLEYE12'**

(50) Latin Name: *Physocarpus opulifolius*
Varietal Denomination: ZLEYe12

(71) Applicant: David Charles Zlesak, River Falls, WI (US)

(72) Inventor: David Charles Zlesak, River Falls, WI (US)

( * ) Notice: Subject to any disclaimer, the term of this patent is extended or adjusted under 35 U.S.C. 154(b) by 97 days.

(21) Appl. No.: 15/732,805

(22) Filed: Jan. 3, 2018

(65) Prior Publication Data

US 2019/0208679 P1 Jul. 4, 2019

(51) Int. Cl.
*A01H 5/02* (2018.01)
*A01H 6/00* (2018.01)

(52) U.S. Cl.
USPC ..... Plt./226
CPC ..... *A01H 6/00* (2018.05); *A01H 5/02* (2013.01)

(58) Field of Classification Search
USPC ..... Plt./226
CPC ..... A01H 5/02
See application file for complete search history.

(56) References Cited

PUBLICATIONS

Plants Nouveau, p. 55, Jul. 9, 2017.*

* cited by examiner

*Primary Examiner* — Keith O. Robinson

(57) ABSTRACT

'ZLEYel2' is a new and distinct cultivar of *Physocarpus opulifolius* plant having an upright, mounded, dense plant habit; compact overall plant size; strong branching characteristics; small yellow-green foliage; short internode length; resistance to powdery mildew; corymbs of small blush-white flowers; coral pink to red follicle color in full sun for about a month after fertilization; and ability to root and grow vigorously from softwood and semi-hardwood cuttings.

3 Drawing Sheets

Latin name of genus and species: *Physocarpus opulifolius.*

Variety denomination: 'ZLEYel2'.

BACKGROUND OF THE INVENTION

The present invention relates to a new and distinct cultivar of *Physocarpus opulifolius* and will be referred to hereafter by its cultivar name, 'ZLEYel2'. *Physocarpus opulifolius* is a deciduous shrub grown for landscape use. The key objective within the *Physocarpus opulifolius* breeding program I initiated in St. Paul, Minn. was to develop new *Physocarpus opulifolius* cultivars that are compact growing, well-branched, healthy, and possess colorful foliage. One objective has been to produce a cultivar with the yellow-green foliage color of *Physocarpus opulifolius* 'Dart's Gold' (not patented) and the compact, well-branched growth habit and small foliage of cultivated ninebark such as *Physocarpus opulifolius* as var. *nanus* (not patented) or its descendant *Physocarpus opulifolius* 'Donna May' (disclosed in U.S. Plant Pat. No. 22,634).

'ZLEYel2' originated by crossing *Physocarpus opulifolius* 'Donna May' as the female parent and *Physocarpus opulifolius* 'Dart's Gold' as the male parent. The pollination that led to the population of seedlings from which 'ZLEYel2' was identified occurred in June 2011. The seeds of this population germinated during the winter of 2011/2012 indoors under florescent lights in St. Paul, Minn. Seedlings were grown in containers during their first year. At the end of the first growing season, seedlings with attractive foliage color, relatively compact growth habits, and powdery mildew resistance were retained. Selections were planted outside during their second growing season. 'ZLEYel2' was recognized as a highly desirable genotype among this seedling population during the summer of 2012. 'ZLEYel2' was planted outside in 2013 and was first asexually propagated using semi-hardwood stem cuttings in the spring of 2013. I have found that the characteristics of 'ZLEYel2' are stable and true to type over successive generations of vegetative propagation.

'ZLEYel2' was unique from the other ninebark seedlings because of its small yellow-green foliage and compact, very well-branched plant habit. 'ZLEYel2' first flowered in 2014 with attractive blush-white flowers that are abundant and attractive against the yellow-green foliage. As follicles develop in full sun, they are a coral pink to red color for about a month and provide additional ornamental value.

SUMMARY OF THE INVENTION

The primary objective of the breeding project was substantially achieved, along with other desirable improvements, as evidenced by the following unique combination of characteristics that are outstanding in the new variety and that distinguish it from its parents, as well as from all other varieties of *Physocarpus opulifolius* of which I am aware:

1. Upright, mounded, dense plant habit;
2. Compact overall plant size;
3. Strong branching characteristics;
4. Small yellow-green foliage;
5. Short internode length;
6. Resistance to powdery mildew;
7. Corymbs of small blush-white flowers;

8. Coral pink to red follicle color in full sun for about a month after fertilization;
9. Ability to root and grow vigorously from softwood and semi-hardwood stem cuttings.

Asexual reproduction of this new cultivar by rooting of softwood and semi-hardwood cuttings, as performed at River Falls and Menomonie Falls, Wis. and St. Paul, Minn. shows that the foregoing and all other characteristics and distinctions come true to form and are established and transmitted through succeeding asexual propagations.

Comparison with Parents

'ZLEYel2' has a similar overall plant size and dense, well branched plant habit as its maternal parent 'Donna May'. The branching of 'ZLEYel2' is slightly more abundant within the plant canopy than 'Donna May' and leads to 'ZLEYel2' having a slightly more dense and slightly more rounded overall plant silhouette than 'Donna May'. Leaf size of 'ZLEYel2' is similar to 'Donna May' with 'ZLEYel2' having slightly wider leaves. Internode length of 'ZLEYel2' is slightly shorter than 'Donna May'. Inflorescence and flower size are similar between 'Donna May' and 'ZLEYel2'. 'ZLEYel2' differs most significantly from 'Donna May' in that the foliage color is yellow-green instead of purple.

'ZLEYel2' has a similar foliage and flower color to its paternal parent, 'Dart's Gold'. It differs from 'Dart's Gold' in that the leaves, stems, internode length, and flowers are all smaller for 'ZLEYel2'. 'ZLEYel2' is more dense and well-branched than 'Dart's Gold' and has an overall smaller plant size than 'Dart's Gold'. Follicle color of 'ZLEYel2' after fertilization and as follicles swell is a more vibrant coral pink to red color and it holds the attractive follicle color longer than 'Dart's Gold'.

Comparison of 'ZLEYel2' with Similar Cultivars

The *Physocarpus opulifolius* cultivar with the greatest similarity to 'ZLEYel2' is *Physocarpus opulifolius* 'SMNPOTWG' (disclosed in U.S. Plant Pat. No. 28,857). Young plants of 'SMPOTWG' were purchased as liners in quart-sized pots in spring 2017. Plants of similar size of 'ZLEYel2' (propagated in 2016) were available and both cultivars were transplanted into 2 gallon pots in spring 2017 and grown without pruning. As of mid-summer 2017 plants of 'ZLEYel2' had more abundant branching originating from axillary buds on current season stems and a much fuller and rounded plant form than 'SMPOTWG'. Foliage size and color were similar between genotypes. A larger, flowering plant in a 2 gallon pot of 'SMPOTWG' was purchased spring 2017 from a local garden center to compare flowering and follicle color. The developing follicles on an older flowering plant in the landscape of 'ZLEYel2' had a stronger coral pink to red coloration than the developing follicles on the potted plant of 'SMPOTWG'. I have not had the opportunity yet to observe a mature specimen of 'SMPOTWG' in a landscape to compare the mature plant size with 'ZLEYel2'.

BRIEF DESCRIPTION OF THE DRAWINGS

The accompanying colored photographs illustrate key features of 'ZLEYel2'. The photographed plant is in its sixth growing season in 2017, the year the photographs were taken. Photographs show the colors as true as it is reasonably possible to obtain with colored reproductions of this type. Colors in the photographs may differ slightly from the color values cited in the detailed botanical description, which accurately describe the colors of 'ZLEYel2'.

DETAILED BOTANICAL DESCRIPTION

Figure 1:
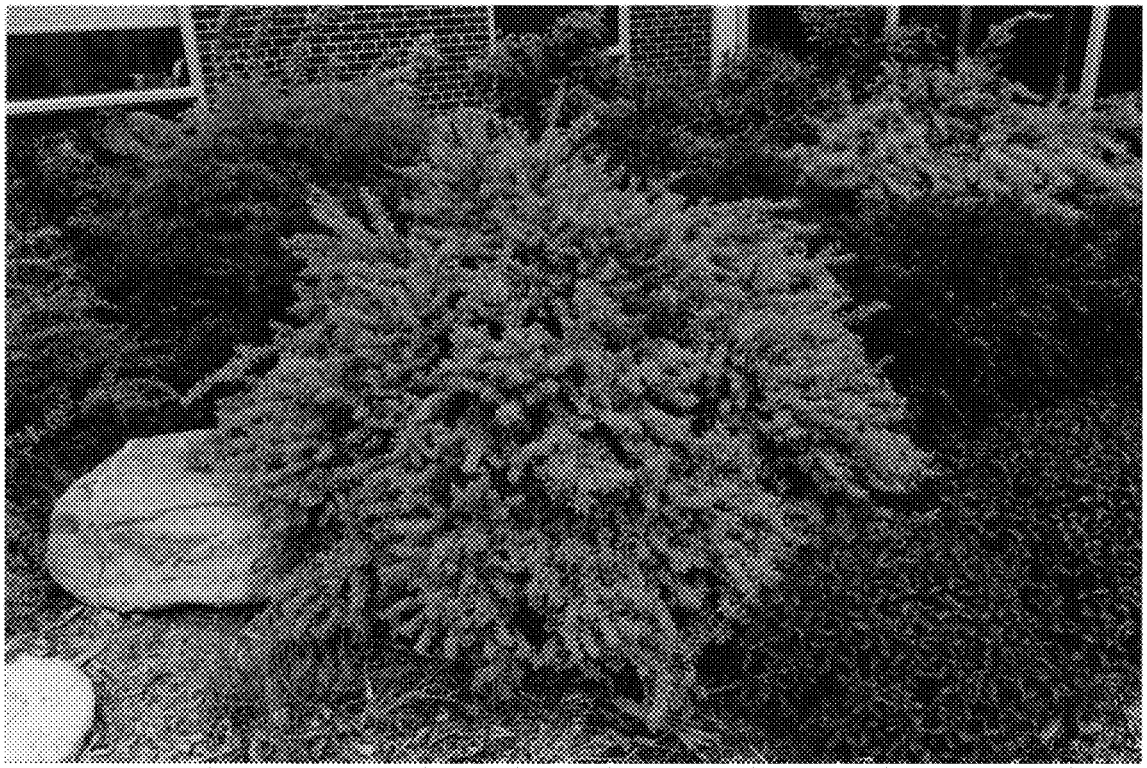
FIG. 1 illustrates a six-year-old plant of 'ZLEYel2' integrated in a landscape with other shrub species before flowering May 2017.
Figure 2:
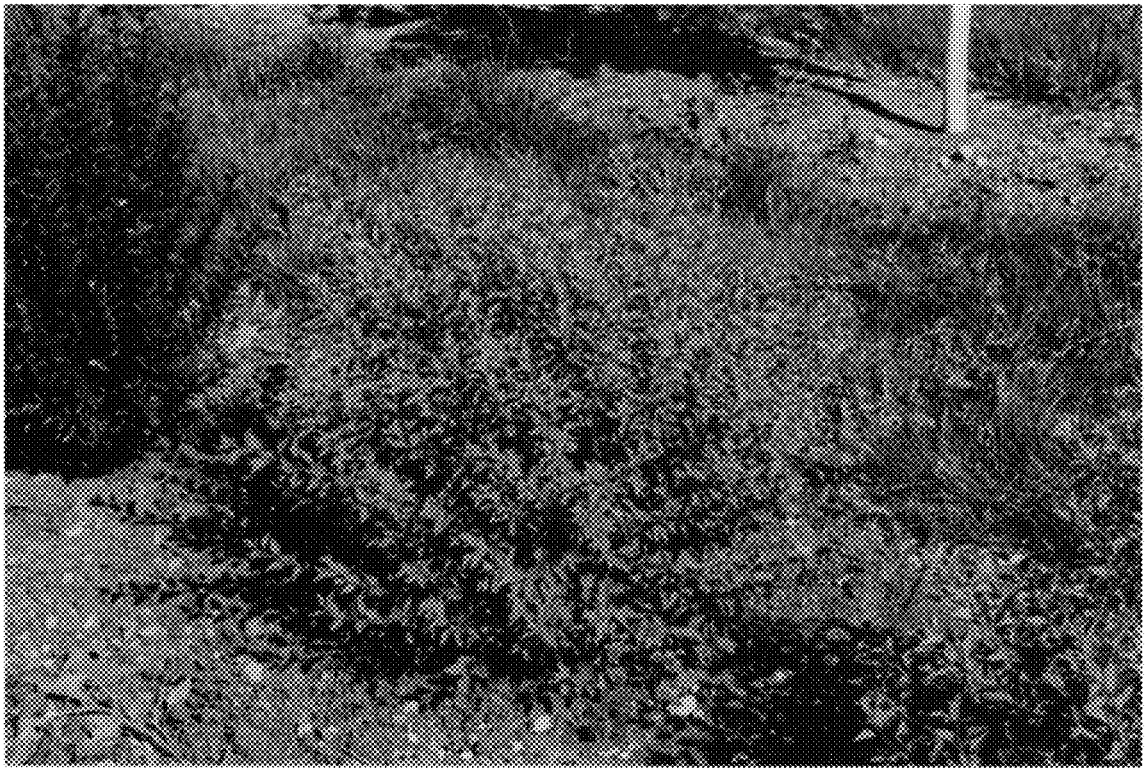
FIG. 2 illustrates a two-year-old plant of 'ZLEYel2' growing in a nursery row in September 2017.
Figure 3:
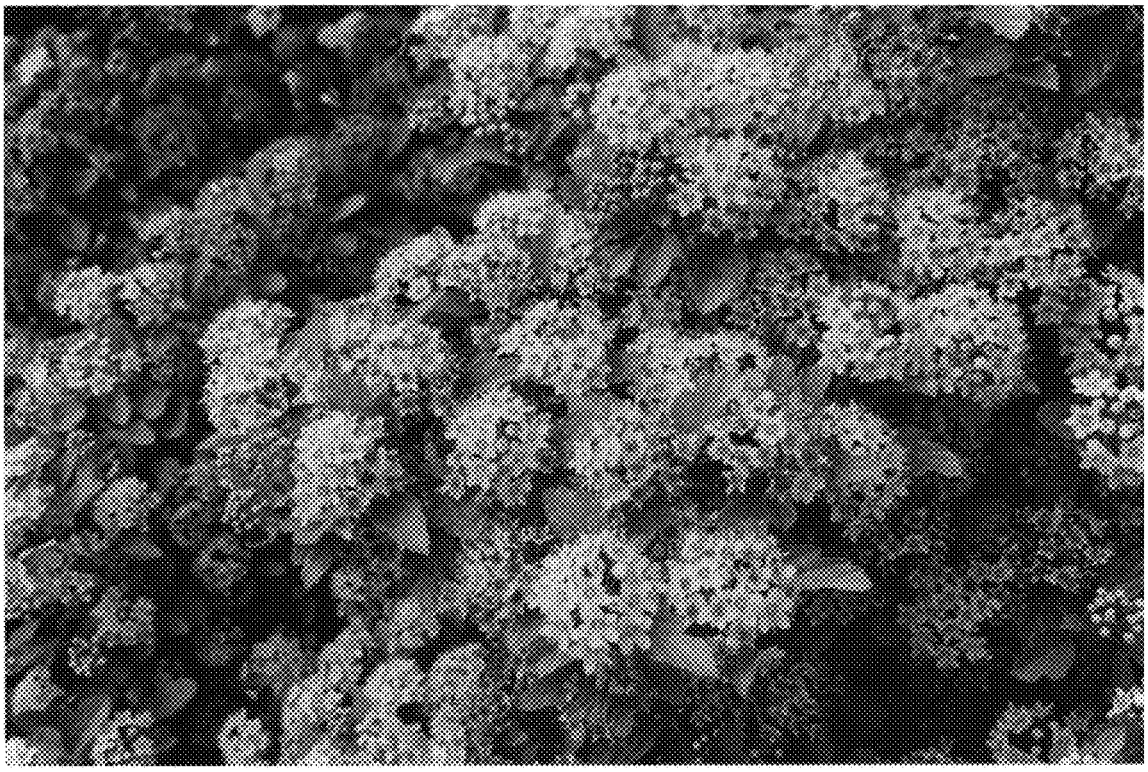
FIG. 3 illustrates corymbs of flowers of 'ZLEYel2' in mid-June 2017.
Figure 4:
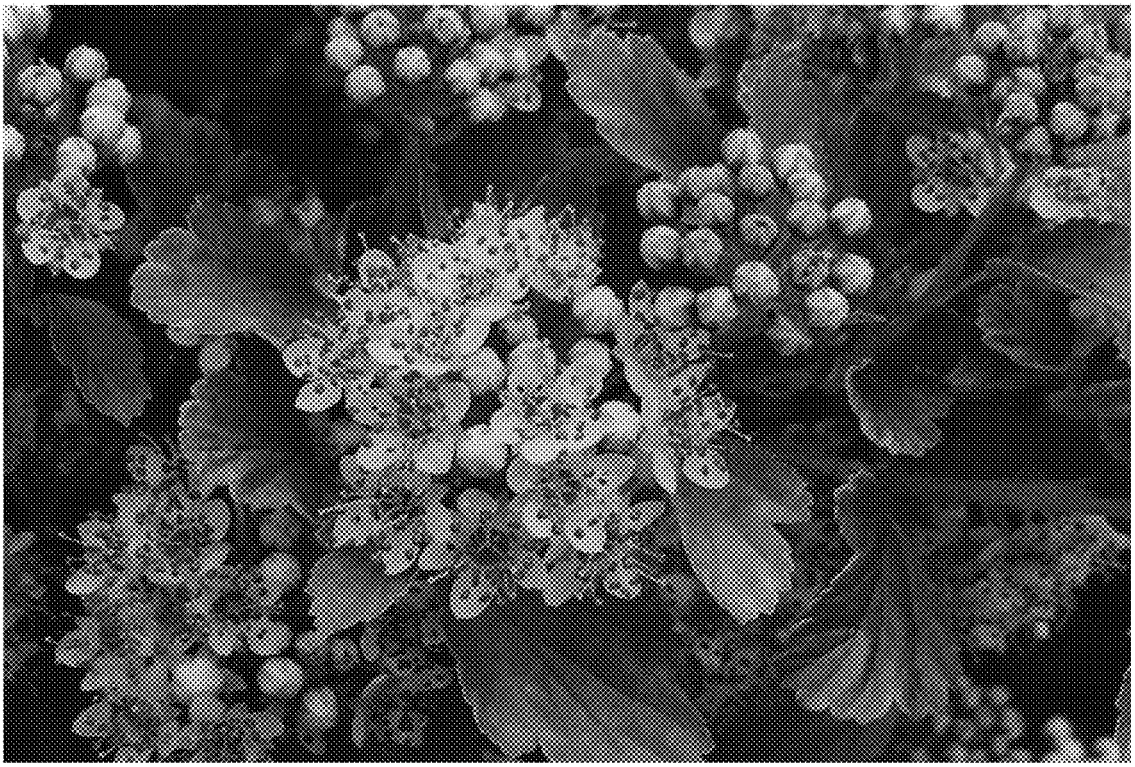
FIG. 4 illustrates a close up of flower buds and open flowers of 'ZLEYel2' in mid-June 2017.
Figure 5:
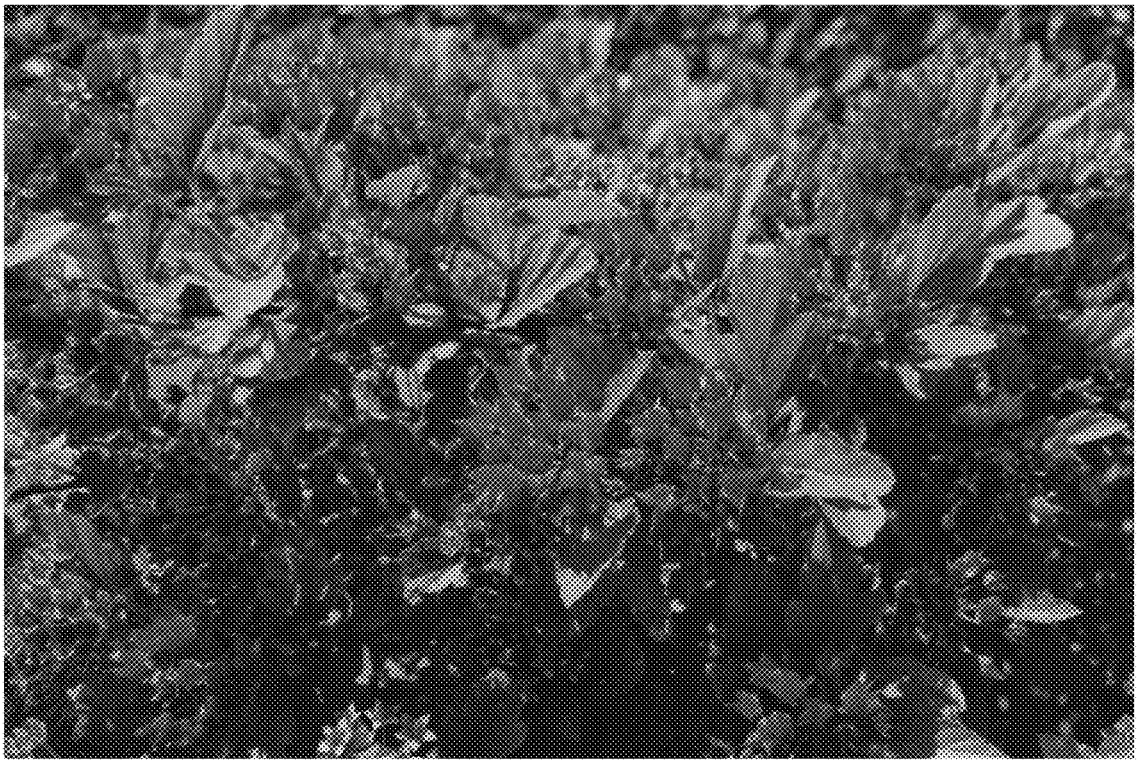
FIG. 5 illustrates developing follicles of 'ZLEYel2' in July 2017.
Figure 6:
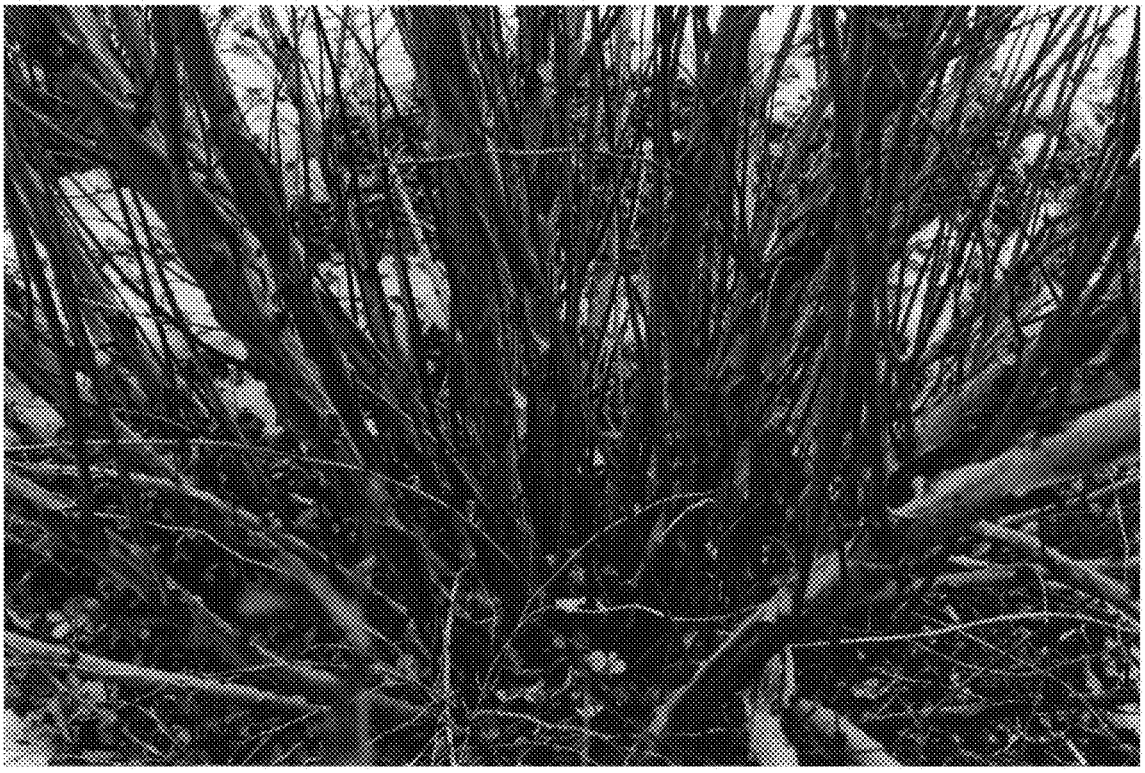
FIG. 6 illustrates stems at the base of a six-year-old plant of 'ZLEYel2' displaying exfoliating bark November 2017.

The following is a detailed description of 'ZLEYel2', the new *Physocarpus opulifolius* cultivar, with color descriptions using terminology in accordance with The Royal Horticultural Society (London) Colour Chart (2001), except where ordinary dictionary significance of color is indicated. The phenotype of the new cultivar may vary with variations in environmental, climatic, and cultural conditions, as it has not been tested under all possible environmental conditions. Descriptions are based on observations of the original seedling during its fifth year of growth in 2016 in River Falls, Wis. and two and three-year-old plants propagated from semi-hardwood cuttings.

Classification:

*Botanical.*—*Physocarpus opulifolius* 'ZLEYel2'.

*Common name of species.*—*Physocarpus* or ninebark.

*Commercial.*—Deciduous shrub.

Parentage:

*Seed parent.*—*Physocarpus opulifolius* 'Donna May' (disclosed in U.S. Plant Pat. No. 22,634).

*Pollen parent.*—*Physocarpus opulifolius* 'Dart's Gold' (not patented).

General description:

*Plant habit.*—Upright, mounded, and compact.

*Plant size.*—1.0-1.3 m in overall height and width.

*Growth habit.*—Vigorous and dense with abundant branching.

*Blooming period.*—About 21 days from mid-June to early July.

*Hardiness.*—Cold hardy to USDA Zone 3.

*Root description.*—Fibrous and vigorous.

*Diseases and pest resistance.*—'ZLEYel2' has shown strong resistance to powdery mildew, even with other ninebarks infected with powdery mildew growing adjacent to it. There are multiple species of fungi that cause powdery mildew on ninebark, and it is unclear which species of fungi were infecting the adjacent, susceptible ninebark genotypes. No other diseases or insect pests of ninebark have been observed on 'ZLEYel2'.

*Cultural requirements.*—'ZLEYel2' does well in full to partial sun and well-drained, moderately fertile soil.

Growth and propagation:

*Propagation.*—Softwood and semi-hardwood stem cuttings have been effective.

*Time required for root initiation and initial development.*—It takes about 3 to 4 weeks during the summer using intermittent mist in the greenhouse without supplemental lighting for cuttings to typically form visible roots.

*Time required to obtain a well-rooted cutting.*—It takes about 6 to 7 weeks to produce a well-rooted cutting in a 2 inch container.

Branch description:

*Branch color.*—The color of current season stems is Yellow-Green Group N144A. Sides of current season's stems in full sun have reddish highlights closest to Red-Purple Group 58A due to the production of anthocyanin pigment. The most mature stems on four-year-old plants had a mixture of colors on the exfoliating bark; primarily Greyed-Orange Group 164A and Greyed-Orange Group 165B, but there were also lighter colored areas close to Greyed-Yellow Group 161A and darker colored areas close to Greyed-Orange 165A.

*Branch size.*—Branches produced during the current season of growth ranged from approximately 15 cm to 60 cm in length and 1 to 4 mm in width. The oldest branches on four-year-old plants were up to 2.0 cm in diameter at the base of the plant.

*Branch surface.*—Young stems: Glabrous with a slight sheen. Older stems: Exfoliating bark layers that are somewhat dull and no longer have a sheen.

*Internode length.*—1.0 to 2.0 cm.

*Branch habit.*—Vigorous current season's stems tend to produce new stems from axillary buds without pruning. This leads to an abundantly branched and dense plant. The angle between the new stems arising from axillary buds and the stem from which they originated is typically 20-60°.

Foliage description:

*Overall leaf size.*—Leaf length is typically about 3.5 cm and leaf width is 1.5-1.75 cm.

*Leaf division.*—Simple.

*Leaf attachment.*—Petiolate.

*Leaf arrangement.*—Alternate.

*Leaf number.*—It varies, but an actively growing branch can easily produce 30-60 leaves in a growing season.

*Leaf blade shape.*—Ovate in overall outline with three prominent lobes.

*Leaf blade base.*—Rounded.

*Leaf blade apex.*—Acute.

*Leaf blade venation.*—Primary venation is palmate with three principal veins. Each principal vein diverges at the juncture of the leaf blade and petiole and travels through the middle of one of the three lobes. Secondary venation off of the three principal veins is pinnate.

*Leaf blade margin.*—The three primarily lobes have secondary undulations or lobes. The margin on the three primary lobes is best described as doubly serrate.

*Leaf blade surface.*—Glabrous on upper and lower surfaces.

*Leaf blade size.*—The leaf blade is approximately 2.5-2.75 cm long and 1.5-1.75 cm wide.

*Leaf blade color.*—Young emerging leaf blades are Yellow-Green Group 153D on the upper and lower surfaces. Young expanded leaf blades are closest to Yellow-Green Group N144A on the upper surface and Yellow-Green Group 146D on the lower surface. Mature leaves are Green Group 137C on the upper surface and Yellow-Green Group 146C on the lower surface.

*Petiole size.*—About 1.0 cm in length and about 1 mm in width.

*Petiole shape.*—Sulcate. The petiole is generally round except for a longitudinal furrow running the length of the upper surface.

*Petiole color.*—Yellow-Green Group 146D.

*Petiole texture.*—Glabrous.

*Stipule number.*—There are two stipules at each node with one on each side of the leaf petiole where it attaches to the stem.

*Stipule size.*—2-3 mm long and 1.25 mm wide.

*Stipule shape.*—Generally lanceolate.

*Stipule color.*—Yellow-Green Group 146D.

Flower description:

*Inflorescence type.*—A corymb with 18-25 rotate flowers arranged in a hemisphere.

*Inflorescence size.*—Typically 1.5-2.0 cm in height and width.

*Inflorescence lastingness.*—The corymb has open flowers typically for up to 21 days with each individual flower open for approximately 3 days.

*Flower bud shape.*—Elliptic to oval.

*Flower bud size and proportions.*—2.5-3.0 mm in length and 2.0 mm in width. The receptacle of the bud accounts for about one half of the proximal end and the calyx accounts for about a half of the distal end of an unopened flower bud.

*Flower bud color.*—The overall color of exposed petal undersides as the sepals open can best be described as White Group 155B. In bright light, there are highlights of Orange-Red Group N34C. The sepals and receptacle are closest to Yellow-Green Group 146C.

*Flower size when fully open.*—4.5-5.5 mm in diameter and 4.0 mm in depth (not including pedicel).

*Flower fragrance.*—Slight and sweet.

*Petal number.*—5.

*Petal size.*—2.0-2.5 mm in length and width.

*Petal shape.*—Elliptic to obovate.

*Petal color.*—Expanding petals are White Group 155B on the upper surface and White Group 155B on the lower surface. The highlights of Orange-Red Group N34C on the petals as the flower buds just start to open are typically no longer present when the petals are fully expanded.

*Sepal number.*—5.

*Sepal size.*—Length is 2.0-3.0 mm and width is 1.0-1.5 mm.

*Sepal shape.*—Deltoid.

*Sepal color.*—Yellow-Green Group 146C.

*Pedicel size.*—The length ranges from about 1.5 cm for the flowers around the perimeter of the corymb to about 0.7 cm for the flowers nearest the terminal or center of the corymb. All pedicels are about 1.0 mm in diameter.

*Pedicel color.*—Yellow-Green Group 146C.

*Subtending bract size.*—There is a subtending bract where each pedicel meets the peduncle of the corymb. The subtending bract is 2.0-3.0 mm long and 1 mm wide below the pedicels at the proximal end of the corymb to 1.0-1.25 mm long and 0.75-1.0 mm wide for the more distal pedicels at the terminal of the corymb.

*Subtending bract shape.*—Elliptic to obovate.

*Subtending bract color.*—Yellow-Green Group 146C.

Gynoecium:

*Pistil number per flower.*—Typically there are 4, but sometimes 3.

*Stigma shape.*—Globular.

*Stigma size.*—0.25 mm in diameter.

*Stigma color.*—Yellow Green Group 146D.

*Style shape.*—Linear.

*Style size.*—About 4 mm long and 0.2 mm wide.

*Style color.*—Yellow Group 145D.

*Ovary shape.*—Elliptic.

*Ovary size.*—About 0.4 mm in length and 0.3 mm in width.

*Ovary color.*—Yellow Green Group 146C.

Androecium:

*Stamen number per flower.*—Approximately 25.

*Anther shape.*—Elliptic to round.

*Anther size.*—0.5 mm in height and width.

*Anther color.*—Red Group 53A.

*Pollen color.*—White Group 155C.

*Pollen abundance.*—Moderate.

*Filament shape.*—Linear.

*Filament size.*—1.0-3.0 mm long and 0.1-0.2 mm wide.

*Filament color.*—Yellow Group 145D.

Fruit and seeds:

*Fruit.*—There are typically three or four firm-walled follicles that form per flower. Follicles can split along both sides of the seam, but split more readily along the inner or adaxial seam. Follicles are elongated and generally ovate in shape with acuminate tips. They are up to 8.0 mm long and approximately 2.0 mm wide. After fertilization and expansion of successfully developing fruit, the surface has a rich vivid coral pink to red color in bright light close to Red-Purple Group N57B. Follicle color tends to be green when out of direct sunlight and near Yellow-Green Group 145D. As the follicles continue to mature the red coloration dissipates. When mature and before turning brown the color is Greyed-Yellow Group 161A. The final color when follicles open and release their seeds is Brown Group 200C.

*Seeds per follicle.*—There are up to 2 seeds per follicle.

*Seed shape.*—Ovate.

*Seed size.*—Up to about 1.75 mm long and 1.25 mm wide.

*Seed color.*—Mature seed color as follicles open and seeds are exposed is closest to Greyed-Orange Group 164A.

Cytology:

*Ploidy.*—Diploid (2n=2x=18). Meristematic root tip cells in the stage of metaphase of mitosis were observed to have 18 chromosomes under a compound microscope at 400× magnification.

Winter hardiness: Acclimated plants of 'ZLEYel2' have displayed strong stem survival (complete survival to minor tip dieback) in United States Department of Agriculture cold hardiness zone 3 and warmer without insulation.

I claim:

1. A new and distinct cultivar of *Physocarpus opulifolius* plant substantially as herein shown and described, characterized particularly by its upright, mounded, dense plant habit; compact overall plant size; strong branching characteristics; small yellow-green foliage; short internode length; resistance to powdery mildew; corymbs of small blush-white flowers; coral pink to red follicle color in full sun for about a month after fertilization; and ability to root and grow vigorously from softwood and semi-hardwood cuttings.

* * * * *